US012080417B2

(12) United States Patent
Lawhorn

(10) Patent No.: US 12,080,417 B2
(45) Date of Patent: Sep. 3, 2024

(54) METHODS AND SYSTEMS FOR MANAGING PATIENT COMPLIANCE

(71) Applicant: Mölnlycke Health Care AB, Gothenburg (SE)

(72) Inventor: Thomas Lawhorn, Norcross, GA (US)

(73) Assignee: Mölnlycke Health Care AB, Gothenburg (SE)

( * ) Notice: Subject to any disclaimer, the term of this patent is extended or adjusted under 35 U.S.C. 154(b) by 130 days.

(21) Appl. No.: 16/463,255

(22) PCT Filed: Feb. 16, 2017

(86) PCT No.: PCT/IB2017/000215
§ 371 (c)(1),
(2) Date: May 22, 2019

(87) PCT Pub. No.: WO2018/096390
PCT Pub. Date: May 31, 2018

(65) Prior Publication Data
US 2019/0295718 A1    Sep. 26, 2019

(51) Int. Cl.
G16H 20/40    (2018.01)
A61M 1/00    (2006.01)
G16H 40/67    (2018.01)

(52) U.S. Cl.
CPC .............. *G16H 40/67* (2018.01); *A61M 1/96* (2021.05); *G16H 20/40* (2018.01); *A61M 2205/18* (2013.01); *A61M 2205/59* (2013.01)

(58) Field of Classification Search
CPC ... G06Q 50/22–24; G16H 40/67; G16H 20/40
See application file for complete search history.

(56) References Cited

U.S. PATENT DOCUMENTS 5,497,772 A * 3/1996 Schulman ............ A61B 5/1495
600/347
6,514,200 B1 * 2/2003 Khouri ................... G16H 10/60
600/300

(Continued)

FOREIGN PATENT DOCUMENTS

WO    WO-2011/0002904 A2    1/2011
WO    WO-2016/061146 A1    4/2016

OTHER PUBLICATIONS

International Search Report and Written Opinion mailed on Aug. 17, 2017 by the International Searching Authority for Patent Application No. PCT/IB2017/000215, which was filed on Feb. 16, 2017 and published as WO 2018/096390 on May 31, 2018 (Inventor—Thomas Lawhorn; Applicant—Mölnlycke Health Care AB) (13 pages).

(Continued)

Primary Examiner — John A Pauls
(74) Attorney, Agent, or Firm — Ballard Spahr LLP

(57) ABSTRACT

Methods and systems for managing patient compliance with a treatment are disclosed. An example method can comprise receiving data indicative of a time on active therapy. The method can comprise receiving data indicative of a pressure associated with the time on active therapy. The method can further comprise determining a patient compliance factor based on the data indicative of the time on active therapy and the data indicative of the pressure associated with the time on active therapy. The method can comprise determining a graphical object modifier based on the patient compliance factor and displaying a graphical object based on the graphical object modifier.

29 Claims, 6 Drawing Sheets

(56) References Cited

U.S. PATENT DOCUMENTS

| | | | | |
|---|---|---|---|---|
| 7,200,779 B1* | 4/2007 | Coss, Jr. | ............. | G06F 11/0709 700/108 |
| 7,933,817 B2* | 4/2011 | Radl | ................... | G07F 17/0014 705/34 |
| 9,805,163 B1* | 10/2017 | Panch | ................... | G16H 10/60 |
| 2003/0110060 A1* | 6/2003 | Clementi | ............... | G16H 20/10 705/2 |
| 2005/0087473 A1* | 4/2005 | Fabricius | ................ | A61J 1/035 206/534 |
| 2005/0197903 A1* | 9/2005 | Hoffman | ................ | G06Q 30/02 705/2 |
| 2007/0219532 A1* | 9/2007 | Karpowicz | ............. | A61M 1/74 604/540 |
| 2010/0022990 A1* | 1/2010 | Karpowicz | ............. | A61M 1/80 604/543 |
| 2011/0077605 A1 | 3/2011 | Karpowicz et al. | | |
| 2011/0153360 A1* | 6/2011 | Hanina | ................ | G16H 20/10 707/E17.014 |
| 2011/0162649 A1* | 7/2011 | Potharaju | .......... | A61M 16/0816 128/203.26 |
| 2012/0165620 A1* | 6/2012 | Tanis | ..................... | G16H 40/63 601/2 |
| 2013/0015975 A1* | 1/2013 | Huennekens | ........ | A61B 5/0084 340/573.1 |
| 2013/0311205 A1* | 11/2013 | Creswell | ................ | G16H 40/60 705/3 |
| 2015/0100335 A1* | 4/2015 | Englehard | ......... | A61M 15/0093 705/2 |
| 2015/0113451 A1* | 4/2015 | Kopp | .................... | G06F 16/242 715/764 |
| 2016/0166464 A1* | 6/2016 | Douglas | ............... | A61H 9/0078 601/148 |
| 2016/0324460 A1* | 11/2016 | Kusens | .................. | A61B 5/447 |
| 2016/0335649 A1* | 11/2016 | Ghosh | ............. | G06Q 10/06393 |
| 2017/0367644 A1* | 12/2017 | Sharman | ............. | A61B 5/1121 |
| 2018/0018372 A1* | 1/2018 | Franke | ............. | G06F 16/24573 |
| 2019/0206226 A1* | 7/2019 | Lindström | ........... | G08B 21/245 |

OTHER PUBLICATIONS

Written Opinion mailed on Jun. 17, 2021, by the Intellectual Property Office of Singapore for Application No. 11201903341R, filed on Feb. 16, 2017 (Inventor—Thomas Lawhom; Applicant—Mölnlycke Health Care AB) (6 pages).

* cited by examiner

US 12,080,417 B2

METHODS AND SYSTEMS FOR MANAGING PATIENT COMPLIANCE

This is a U.S. National Phase Application of International Application No. PCT/IB2017/000215, filed Feb. 16, 2017, which claims the benefit of U.S. Provisional Application No. 62/425,758 filed on Nov. 23, 2016, which are both incorporated herein by reference in their entireties.

SUMMARY

It is to be understood that both the following general description and the following detailed description are exemplary and explanatory only and are not restrictive, as claimed. Provided are methods and systems for managing patient compliance with a treatment. In an aspect, an example method can comprise receiving (e.g., by a negative pressure wound treatment apparatus) data indicative of a time on active therapy. The method can comprise receiving (e.g., by the negative pressure wound treatment apparatus) data indicative of a pressure associated with the time on active therapy. The method can further comprise determining (e.g., by the negative pressure wound treatment apparatus) a patient compliance factor based on the data indicative of the time on active therapy and the data indicative of the pressure associated with the time on active therapy. The method can comprise determining (e.g., by the negative pressure wound treatment apparatus) a graphical object modifier based on the patient compliance factor and displaying a graphical object based on the graphical object modifier.

In another aspect, an example method can comprise receiving (e.g., by a negative pressure wound treatment apparatus) data indicative of a time on active therapy, receiving (e.g., by the negative pressure wound treatment apparatus) data indicative of a pressure associated with the time on active therapy. The method can comprise determining (e.g., by the negative pressure wound treatment apparatus) a patient compliance factor based on the data indicative of the time on active therapy and the data indicative of the pressure associated with the time on active therapy. The method can comprise transmitting (e.g., by the negative pressure wound treatment apparatus) an alert indicative of the patient compliance factor to one or more remote computing devices.

In another aspect, an example apparatus can comprise a wound cover configured for creating a sealable space defined in part by a wound surface and a vacuum pump, coupled to the wound cover though a tube. The vacuum pump can be configured to apply negative pressure to the sealable space through the tube. The apparatus can comprise a processor, in electronic communication with the vacuum pump. The processor can be configured to determine a state of the vacuum pump, determine an amount of the applied negative pressure of the vacuum pump, determine a patient compliance factor based on the state of the vacuum pump and the amount of the applied negative pressure, and determine a graphical object modifier based on the patient compliance factor. The apparatus can comprise a display, in electronic communication with the processor, configured to display a graphical object based on the graphical object modifier.

Additional advantages will be set forth in part in the description which follows or may be learned by practice.

The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
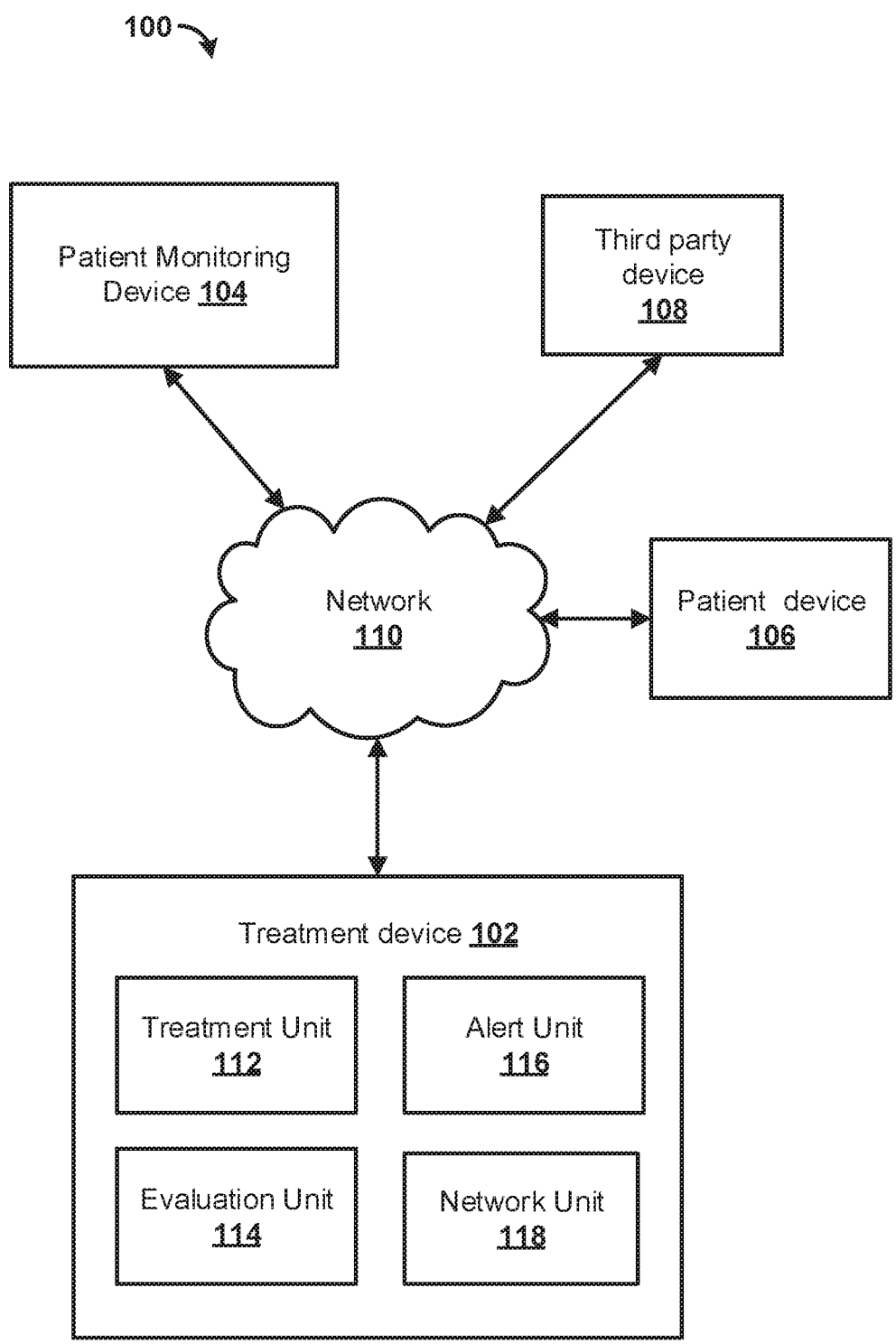
FIG. 1 is a block diagram illustrating an example system for managing treatment of a patient.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present disclosure relates to methods, systems, and an apparatus for managing treatment of a patient. For example, a treatment such as a therapy can be prescribed for a patient. The treatment can comprise applying a device, such as a negative pressure wound treatment apparatus, to a portion of the patient. The treatment, however, may only be effective if it is applied properly. For example, the device may fail to properly apply treatment because of inadequate dressing seal, connectors being disconnected, damaged system components resulting in air leaks into the system, battery depletion, AC power disconnected, and/or the like. As another example, a user may fail to operate the device properly or fail to apply the treatment according to prescribed schedule. Accordingly, operation parameters related to the treatment can be defined, measured, analyzed, and/or the like to determine whether the treatment is being applied. For example, the amount of pressure and amount of time the negative pressure wound treatment apparatus is applied can be measured and analyzed to determine a patient compliance factor. An indicator (e.g., alert), such as a graphical object, light, and/or sound can be provided to notify the patient and/or other parties (e.g., health care provider, third party) regarding patient compliance with the treatment plan. The indicator can be further modified (e.g., updated, replaced) to show the patient's continuing compliance or failure to comply with the treatment.

FIG. 1 is a block diagram illustrating an example system 100 for managing treatment of a patient. In an aspect, the system 100 can comprise one or more devices, such as a treatment device 102, a patient monitoring device 104, a patient device 106, and a third party device 108.

In one aspect, system 100 can comprise a network 110. In one aspect, the network 110 can comprise a packet switched network (e.g., internet protocol based network), a non-packet switched network (e.g., quadrature amplitude modulation based network), and/or the like. The network 110 can comprise network adapters, switches, routers, modems, and the like connected through wireless links (e.g., radio frequency, satellite) and/or physical links (e.g., fiber optic cable, coaxial cable, Ethernet cable, or a combination thereof). The network 110 can comprise public networks, private networks, wide area networks (e.g., Internet), local area networks, and/or the like. In one aspect, the network 110 can be configured to provide communication from telephone, cellular, modem, and/or other electronic devices to and throughout the system 100. For example, the network 110 can be configured to communicatively couple one or more of the treatment device 102, the patient monitoring device 104, the patient device 106, and the third party device 108, and/or the like.

Figure 2:
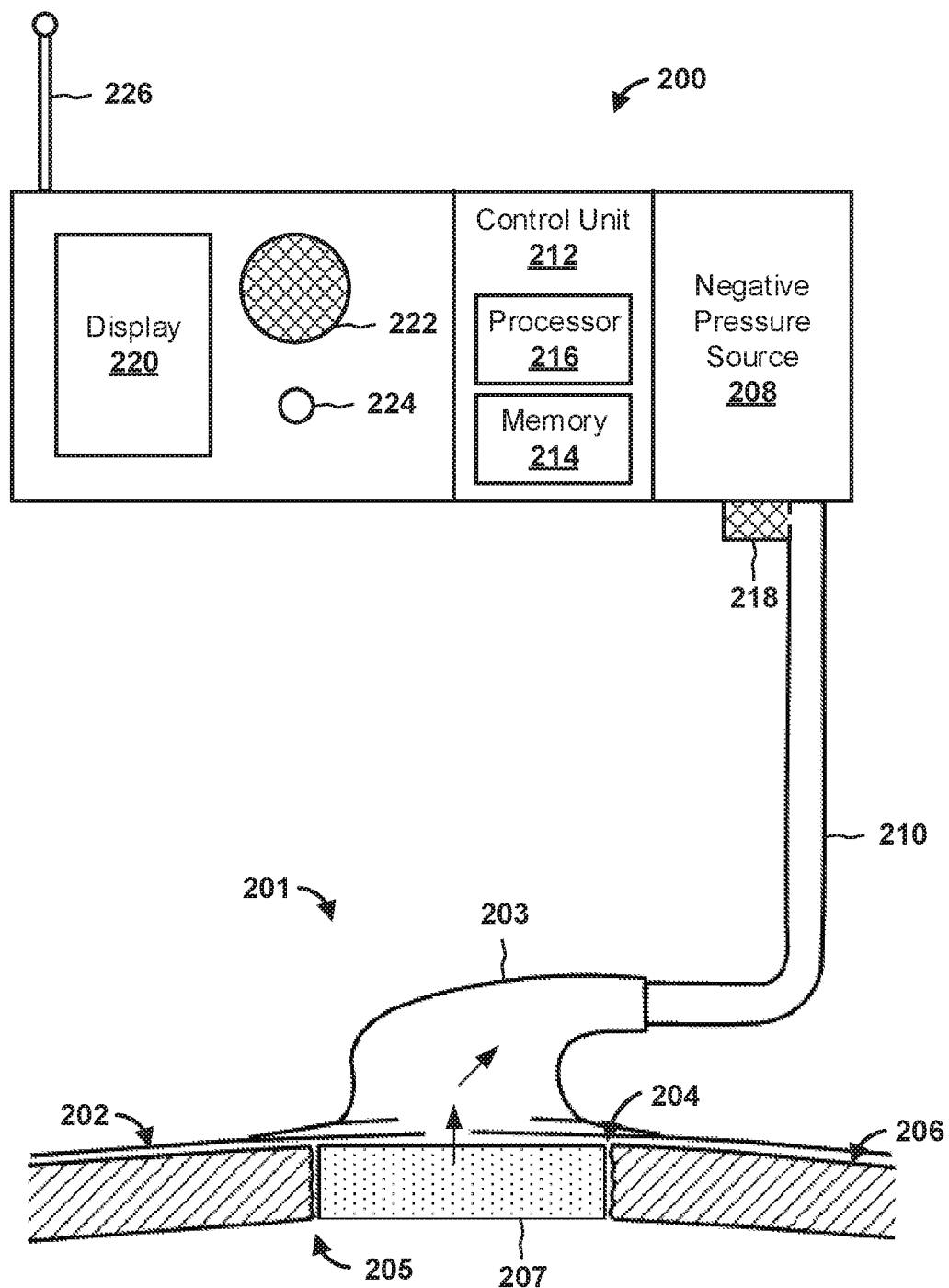
FIG. 2 is a side view of an example treatment device.

In an aspect, the treatment device 102 can be configured to apply a treatment to a patient. The treatment device 102 can comprise a treatment unit 112 configured to apply a treatment (e.g., therapy) to the patient. For example, the treatment unit 112 can apply any type of physical therapy, such as movement, stretching, compression, heat, cold, fluid injection, fluid removal, pressure, negative pressure, radiation, chemical application or injection, dispersing of a pill, measurement of vitals, and/or the like. As an illustration, the treatment unit 112 can be configured to apply a negative pressure wound therapy, as illustrated in FIG. 2 and described further herein. For example, the treatment unit 112 can comprise a negative pressure source (e.g., pressure pump, vacuum pump) configured to create negative pressure. The negative pressure can be communicated to a wound of the patient via a tubing and a treatment pad affixed to the patient.

In an aspect, the treatment device 102 can be configured to evaluate (e.g., assess, analyze) the treatment. For example, the treatment device 102 can comprise an evaluation unit 114 configured to determine when the treatment is being applied, whether the treatment is being applied properly (e.g., within specified operation parameters), and/or the like. For example, the evaluation unit 114 can determine whether treatment of the patient is in compliance with a treatment plan. The evaluation unit 114 can determine a patient compliance factor. The patient compliance factor can comprise a measure of and/or be indicative of compliance with the treatment plan (e.g., schedule). For example, the treatment plan can be a prescribed treatment plan (e.g., prescribed or ordered by a health care professional). The treatment plan can comprise specific times (e.g., start times, end times, duration) for applying a treatment and the frequency or duration of breaks (e.g., number and length of time periods when the treatment device 102 is not used). The treatment plan can comprise an amount of time to apply the treatment during a time period. The treatment plan can comprise operation parameters for applying the treatment via the first device. The operation parameters can comprise a pressure level (e.g., negative pressure level), air flow, power level, configuration settings (e.g., signal to use to apply negative pressure), and/or the like.

In an aspect, the evaluation unit 114 can be configured to track one or more of the operation parameters. For example, the evaluation unit 114 can comprise one or more sensors, such as a power sensor, an air flow sensor, a pressure sensor, a radiation sensor, a fluid sensor, a pill counter, a temperature sensor, a chemical sensor, an accelerometer, and/or the like. As an illustration, the one or more sensors can comprise a pressure sensor configured to detect presence and/or an amount of positive and/or negative pressure. The evaluation unit 114 can continuously and/or periodically measure the one or more operation parameters via the one or more sensors. Measurements can be stored in local or remote data store, such as a database. The evaluation unit 114 can be configured to associate the measurements with corresponding timestamps (e.g., determined based on an internal or external clock). For example, the evaluation unit 114 can be configured to associate a first periodic timestamp with the state of the negative pressure source (e.g., vacuum pump). The evaluation unit 114 can be configured to associate a second periodic timestamp with the amount of an applied negative pressure.

In an aspect, the evaluation unit 114 can be configured to determine a state of the treatment device 102 (e.g., treatment unit 112, vacuum pump). Example states can comprise an active state, an inactive state, and a partially active state. For example, a partially active state can comprise a state in which the treatment device 102 is operating or being applied outside (e.g., not according to) the prescribed operation parameters (e.g., below prescribed pressure). An inactive state can comprise a state in which the treatment device 102 is not operating (e.g., turned off, paused) and/or not applying treatment to the patient. An active state can comprise a state in which the treatment device 102 is operating within (e.g., according to) the prescribed operation parameters (e.g., above the prescribed pressure).

The evaluation unit 114 can be configured to determine one or more cause indicators related to operation of the treatment device 102. The cause indicators can indicate a cause for the state of the treatment device 102. Example cause indicators can be indicative of at least one of the vacuum being switched off or paused, an air leakage, a loss of power, a canister not being engaged, the canister being full, an air blockage, a system error, a reduced vacuum pressure level, a combination thereof, and/or the like.

The evaluation unit 114 can store, associate, and/or the like one or more states of the treatment device 102, timestamps, cause indicators, and/or the like in the data store. For example, the data store can associate a timestamp (e.g., periodic timestamp), the state (e.g., active, inactive, partially active) of the treatment device 102, and a cause indicator.

The evaluation unit 114 can be configured to determine the patient compliance factor based on the state of the negative pressure source (e.g., vacuum pump) and/or the amount of the applied negative pressure. A first periodic timestamp can be determined and/or associated with the state of the negative pressure source. A second periodic timestamp can be determined and/or associated with the amount of the applied negative pressure. The first periodic timestamp can be matched with the second periodic timestamp. If the first periodic timestamp matches the second periodic timestamp, the evaluation unit 114 can determine if the state of the negative pressure source associated with the first periodic timestamp is an active state. The evaluation unit 114 can also determine if the pressure applied by the negative pressure source associated with the second periodic timestamp is within a prescribed pressure. If the state of the negative pressure source associated with the first periodic timestamp is an active state and if the pressure applied by the negative pressure source associated with the second periodic timestamp is within the prescribed pressure, the evaluation unit 114 can update the patient compliance factor to indicate positive patient compliance. If the state of the negative pressure source associated with the first periodic timestamp is an inactive state or if the pressure applied by the negative pressure source associated with the second periodic timestamp is not within the prescribed pressure, the evaluation unit 114 can update the patient compliance factor to indicate negative patient compliance. In an aspect, when the evaluation unit 114 determines that the treatment device 102 is in an inactive state, the information can be logged (e.g., stored in memory) by the evaluation unit 114 and can then be used to update the patient compliance factor. The updated patient compliance can be a certain percentage change or increased/decreased level of magnitude different than the previous patient compliance factor. For example, the change in the updated patient compliance factor can be determined by comparing the total time in a 24-hour period in which the treatment device 102 is in an active state with data showing the total time in a 24-hour period in which a similar treatment device used by similarly situated patients (e.g., demographics, age, gender, weight, wound volume, wound area, wound drainage amounts, and the like) was in an active state on average throughout the course of treatment. For example, a patient with a higher average active time per 24-hour period may heal in a shorter timeframe than a patient with a lower average active time per 24-hour period. Additionally, or in the alternative, the change in the updated patient compliance factor can be determined by comparing the total time in a 24-hour period in which the treatment device 102 is in an active state with data previously collected and stored by the evaluation unit 114 (e.g., previous 24-hour period, previous 3-day period, previous week, and the like).

In a further aspect, when the evaluation unit 114 determines that the pressure applied by the negative pressure source is not within the prescribed pressure, the pressure level and duration of time the negative pressure source is not within the prescribed pressure can be logged (e.g., stored in memory) by the evaluation unit 114 and then used to update the patient compliance factor. The updated patient compliance can be a certain percentage change or increased/decreased level of magnitude different than the previous patient compliance factor. For example, the change in the updated patient compliance factor can be determined by comparing the pressure level and duration of time a negative pressure source was not within the prescribed pressure for similarly situated patients (e.g., demographics, age, gender, weight, wound volume, wound area, wound drainage amounts, and the like) throughout the course of treatment. For example, a patient with a lower overall frequency and/or magnitude of drops in pressure throughout treatment may heal in a shorter timeframe than a patient with a higher overall frequency and/or magnitude of drops in pressure throughout treatment. Additionally, or in the alternative, the change in the updated patient compliance factor can be determined by comparing the pressure level and duration of time a negative pressure source was not within the prescribed pressure with data previously collected and stored by the evaluation unit 114 (e.g., previous 24-hour period, previous 3-day period, previous week, and the like).

The evaluation unit 114 can be further configured to determine the patient compliance factor based on the frequency and duration of time periods in which the treatment device 102 is in an inactive state (e.g., the treatment device is turned off, paused, and/or not applying treatment to the patient). Determining whether the treatment device 102 is in an inactive state can comprise the following steps: A first periodic timestamp can be determined and/or associated with a state of the negative pressure source. A second periodic timestamp can be determined and/or associated with the amount of the applied negative pressure. The first periodic timestamp can be matched with the second periodic timestamp. If the first periodic timestamp matches the second periodic timestamp, the evaluation unit 114 can determine if the state of the negative pressure source associated with the first periodic timestamp is an inactive state. If the state of the negative pressure source associated with the first periodic timestamp is an inactive state, the evaluation unit 114 can log (e.g., store in memory) the time and duration of the inactive state. The evaluation unit 114 can determine whether the treatment device 102 is in an inactive state multiple times per day. The information logged (e.g., stored in memory) by the evaluation unit 114 can then be used to update the patient compliance factor. The updated patient compliance can be a certain percentage change or increased/decreased level of magnitude different than the previous patient compliance factor. In an aspect, the change in the updated patient compliance factor can be determined by comparing the frequency and duration of time periods in which the treatment device 102 is in an inactive state with data showing the frequency and duration of time periods in which a similar treatment device used by similarly situated patients (e.g., demographics, age, gender, weight, wound volume, wound area, wound drainage amounts, and the like) was in an inactive state throughout the course of treatment. For example, a patient with a lower number of inactive states in a 24-hour period, or with shorter duration of inactive states in a 24-hour period, may heal in a shorter timeframe than a patient with a higher number, or lengthier number, of inactive states throughout the course of treatment. Additionally, or in the alternative, the change in the updated patient compliance factor can be determined by comparing the frequency and duration of time periods in which the treatment device 102 is in an inactive state with data previously collected and stored by the evaluation unit 114 (e.g., previous 24-hour period, previous 3-day period, previous week, and the like).

The evaluation unit 114 can be further configured to determine the patient compliance factor based on the change in wound volume. The wound volume can be determined, for example, by measuring the amount of fluid the treatment device transports between the wound and a negative pressure source. The wound volume information can be logged (e.g., stored in memory) by the evaluation unit 114 and then be used to update the patient compliance factor. The updated patient compliance can be a certain percent different than the previous patient compliance factor. For example, the change in the updated patient compliance factor can be determined by comparing the change in wound volume during a specific time period with data showing the change in wound volume over the same length of time for similarly situated patients (e.g., demographics, age, gender, weight, injury type, cause of wound, wound area, wound drainage amount, and the like) using a similar treatment device. As an example, a patient with a greater change in wound volume during a specific time period may heal in a shorter timeframe than a patient with a lesser change in wound volume over the same length of time. Additionally, or in the alternative, the change in the updated patient compliance factor can be determined by comparing the change in wound volume during a specific time period with data previously collected and stored by the evaluation unit 114 (e.g., previous 24-hour period, previous 3-day period, previous week, and the like).

Figure 3A:
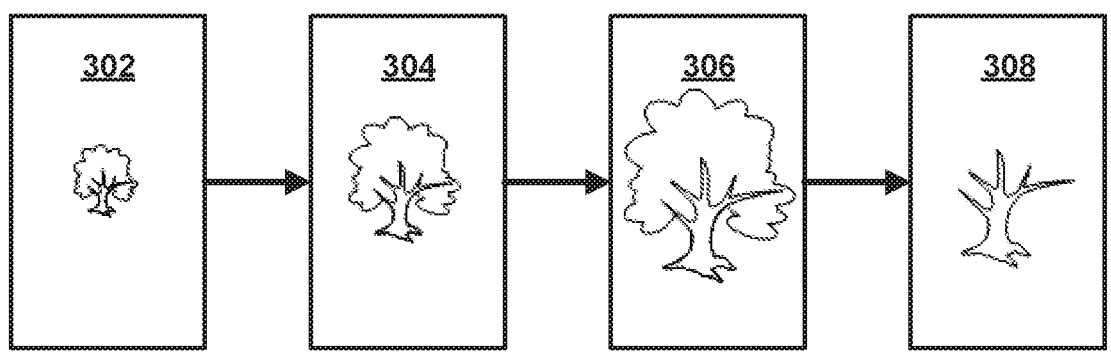
FIG. 3A illustrates modification of an example graphical object.
Figure 3B:
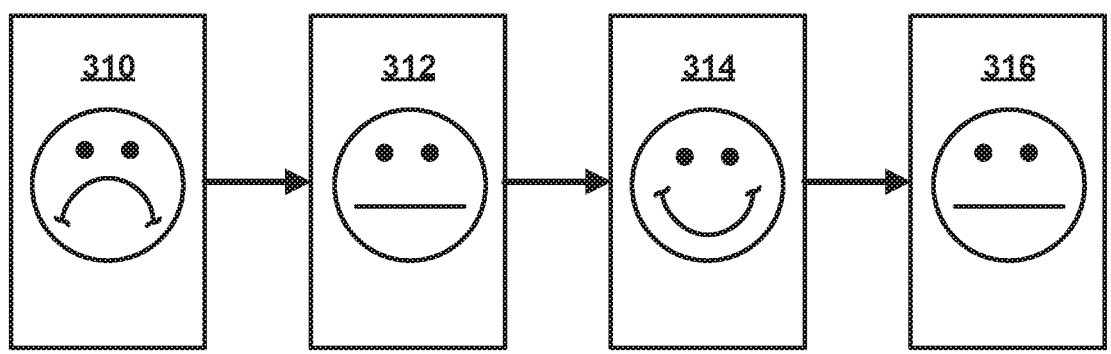
FIG. 3B illustrates modification of another example graphical object.

In an aspect, the treatment device 102 can comprise an alert unit 116. The alert unit 116 can be configured to provide an alert or other notification indicating the status of the treatment. For example, the alert can be provided (e.g., communicated, transmitted) via an audio signal, a light indicator, a graphical object, and/or the like. For example, the alert can be communicated by adjusting one or more parameters indicative of one or more of, a size, a color, and a shape of the graphical object. For example, the graphical object can be increased or decreased in size. The graphical object can be progressed or digressed in maturity. For example, if the graphical object comprises a plant (e.g., tree, flower), the graphical object can appear to grow (e.g., if the patient is compliant) and/or wither or shrink (e.g., if the patient is not compliant), as shown in FIG. 3A. For example, data collected by the evaluation unit 114 can be compared to similarly situated patients, and the comparison can yield a factor by which the graphical object, such as a tree, grows (e.g., taller or more leaves) or withers (e.g., shorter or less leaves). In an aspect, the evaluation unit 114 can log the frequency and duration of time periods in which the treatment device 102 is in an inactive state, and the logs can be compared with data taken from similarly situated patients. If, for example, the patient has 20% more time periods in which the treatment device 102 is in an inactive state as compared to the average of similarly situated patients, then the tree could be displayed as 20% shorter or with 20% less leaves than the way in which it was previously displayed. In another aspect, the evaluation unit 114 can log the total time in a 24-hour period in which the treatment device 102 is in an active state, and the logs can be compared with data taken from similarly situated patients. If, for example, the patient uses the treatment device 102 10% more in 24-hour period as compared to the average time of use in a 24-hour period of similarly situated patients, then the tree could be displayed as 10% taller or with 10% more leaves than the way in which it was previously displayed. In a further aspect, the evaluation unit 114 can log frequency and duration of time periods in which the pressure applied by the negative pressure source is not within the prescribed pressure, and the data logged can be compared with data taken from similarly situated patients. If, for example, the pressure applied by the negative pressure source is 5% less time on average in a 24-hour period as compared to the average pressure level of similarly situated patients in a 24-hour period, then the tree could be displayed as 5% shorter or with 5% less leaves than the way in which it was previously displayed. In yet another aspect, wound volume information can be logged (e.g., stored in memory) by the evaluation unit 114 and then compared with data taken from similarly situated patients. If, for example, the wound volume decreases 1% more in a 24-hour period as compared to the average wound volume change for situated patients in a 24-hour period, then the tree could be displayed as 1% higher or with 1% more leaves than the way in which it was previously displayed. If the graphical object represents a face, the graphical object can be modified in a manner similar to modifying a graphically displayed plant, above, to express happiness, sadness, and/or have a neutral expression, as illustrated in FIG. 3B. In another aspect, the graphical object can be a circle (or any other shape, for example a square, a triangle, a rectangle/column, and the like) that is formed as the patient continues to be compliant. The circle can also regress in a manner similar to modifying a graphically displayed plant, above, if the patient is not compliant. For example, the circle can be made up of a plurality of segments. As patient compliance continues, the plurality of segments sequentially display (e.g., "light up"), ultimately forming a complete circle. Conversely, if the patient is not compliant, the plurality of segments can sequentially disappear, ultimately resulting in no circle being displayed. In another aspect, the graphical object can be one or more LED lights. The one or more LED lights can indicate patient compliance by increasing/decreasing brightness and/or color in a manner similar to modifying a graphically displayed plant, above. In a further aspect, the plurality of segments of the circle (or any other shape) can each comprise one or more LED lights.

In an aspect, the alert can be indicative of the patient compliance factor. For example, the alert unit 116 can be configured to determine a severity of the patient compliance factor. The alert can be adjusted (e.g., or selected) to indicate the severity of the patient compliance factor. By way of explanation, determining the severity of the patient compliance factor can comprise performing one or more of the following steps in any appropriate order. In a first step, it can be determined if the patient compliance factor indicates a negative compliance or a positive compliance. In a second step, a length of time the patient compliance factor has indicated a negative compliance or a positive compliance can be determined. In a third step, it can be determined that the patient compliance factor indicates a high risk if the patient compliance factor indicates a negative compliance and the length of time the patient compliance factor has indicated a negative compliance exceeds a predetermined threshold. It can be determined that the patient compliance factor indicates a low risk if the patient compliance factor indicates a positive compliance and the length of time the patient compliance factor has indicated a positive compliance exceeds a predetermined threshold.

In an aspect, the treatment device 102 can be configured to provide (e.g., transmit) the alert (e.g., or data representing the alert) to one or more remote computing devices and/or one or more recipients. The alert unit 116 can be configured to select one or more recipients based on the severity of the patient compliance factor. For example, if the severity is above a threshold, the recipients can comprise the patient, a health care provider, a third party (e.g., relative, neighbor, police department, emergency service), and/or the like. If the severity is below a threshold, the recipients can comprise the patient, the healthcare provider, and/or the like.

The alert unit 116 can be configured to identify a mode of communication associated with one or more (or each) of the selected one or more recipients. For example, if the only recipient is the patient, the mode of communication can comprise providing the alert via the treatment device 102. As another example, if the recipients includes a remote health care provider and/or a third party, the mode of communication can comprise a network signal, such as a wireless (e.g., WiFi, Bluetooth®, cellular) signal. In some implementations, a wireless signal can be provided to the patient device 106. The alert unit 116 can be configured to send a control signal to a network unit 118 to transmit the alert to the selected one or more recipients according to the associated mode of communication.

In an aspect, the alert unit 116 can be configured to modify (e.g., adjust, replace) the graphical object. For example, the alert unit 116 can be configured to determine a graphical object modifier. The graphical object modifier can be determined based on the patient compliance factor, the severity of the patient compliance factor, whether the patient compliance factor is negative or positive, and/or the like. The graphical object modifier can be determined by accessing (e.g., adjusting, selecting, modifying) one or more parameters indicative of one or more of, a size, a color, and a shape of the graphical object. Examples of modifying the graphical object are illustrated in FIG. 3A and FIG. 3B.

In an aspect, the treatment device 102 can comprise a network unit 118. As an example, the network unit 118 can request or query various files from a local source and/or a remote source. As a further example, the network unit 118 can transmit and/or receive data to a local or remote device such as the patient monitoring device 104. The network unit 118 can comprise hardware and/or software to facilitate communication. For example, the network unit 118 can comprise one or more of a modem, transceiver (e.g., wireless transceiver)), digital-to-analog converter, analog-to-digital converter, encoder, decoder, modulator, demodulator, tuner (e.g., QAM tuner, QPSK tuner), and/or the like. In one aspect, the network unit 118 can be configured to allow one or more remote devices (e.g., in a local or remote portion of the network 110) to control operation of the treatment device 102.

In an aspect, the patient monitoring device 104 can be configured to allow a health care provider to manage the treatment of the patient. The patient monitoring device 104 can be located proximate to (e.g., in the same room) or remotely (e.g., in another room of a building, at an offsite location) from the treatment device 102.

The patient monitoring device 104 can be configured to communicate with a plurality of treatment devices, such as the treatment device 102. The patient monitoring device 104 can receive data (e.g., state, operation parameters, alerts) from the treatment device 102. The patient monitoring device 104 can analyze the data and generate one or more messages to health care providers, such as a doctor, nurse, and/or support staff associated with the patient. The patient monitoring device 104 can be configured to receive a treatment plan and/or an update to a treatment plan from the health care provider. The patient monitoring device 104 can provide the treatment plan to the treatment device 102, patient device 106, and/or the third party device 108. The patient monitoring device 104 can alert a third party (e.g., emergency service) to visit the patient and/or provide other messages to devices in the network 110.

In an aspect, the patient device 106 can be configured to allow the patient to manage treatment. The patient device 106 can comprise a computer, a smart device (e.g., smart phone, smart watch, smart glasses, smart apparel, smart accessory), a laptop, a tablet, a set top box, a display device (e.g., television, monitor), digital streaming device, transportation device (e.g., on board computer, navigation system, vehicle media center), and/or the like.

In one aspect, the patient device 106 can be configured to provide an interface to a user to interact with the patient device 106 and/or remote devices, such as the treatment device 102, the patient monitoring device 104, and/or the third party device 108. The interface can comprise any interface for presenting and/or receiving information to/from the user, such as user feedback. An example interface can comprise a content viewer, such as a web browser (e.g., Internet Explorer®, Mozilla Firefox®, Google Chrome®, Safari®, or the like), media player, application (e.g., web application, mobile application, media device application), and/or the like.

For example, the interface can comprise an application configured to control the treatment device 102, communicate with a health care provider, receive alerts from the treatment device 102 and/or health care provider, store data (e.g., measurements, timestamps, compliance factors) from the treatment device 102, and/or the like. For example, the patient device 106 can receive treatment plans and/or updates to treatment plans from the health care provider (e.g., from the patient monitoring device 104).

In an aspect, the third party device 108 can be configured to allow a third party to manage treatment of the patient. An example third party can comprise a relative, neighbor, emergency service (e.g., ambulance, fire department, police department), health care record storage company, and/or the like. The third party device 108 can be configured to receive data and/or alerts from treatment device 102, patient monitoring device 104, patient device 106 and/or the like. For example, the patient can specify a third party to notify when a condition is triggered, such as the severity being above a threshold value.

FIG. 2 is a side view of an example treatment device 200. In an aspect, the treatment device 200 can comprise a negative pressure wound therapy apparatus configured to apply a negative pressure to a wound 205 of a patient.

The treatment device 200 can comprise a fluid communication assembly 201. The fluid communication assembly 201 can comprise a suction member 203 (e.g., suction cup). The suction member 203 can be configured to communicate a pressure (e.g., negative pressure) to the wound 205. The fluid communication assembly 201 can comprise a wound cover 202 configured for creating a sealable space 204 defined in part by a wound surface 206. The wound cover 202 can be configured to be attached to the skin surrounding the wound 205. For example, the wound cover 202 may comprise a wound cover film. The wound cover 202 may preferably be attached to the skin surrounding the wound 205, for instance by means of an adhesive. Examples of adhesives that may be used include, but are not limited to, acrylic adhesives and/or silicone gel adhesives. In an aspect, the adhesive or adhesives can be incorporated as part of the wound cover film. In another aspect, the adhesive or adhesives can be applied to the wound cover 202 during use. By way of example, the adhesive sold under the trademark Mepiseal® by Molnlycke Healthcare AB may be used for attaching the wound cover 202 to the skin surrounding the wound 205.

The treatment device 200 can comprise a wound filler 207. The wound filler 207 can comprise an absorbent material, a flexible material, and/or the like such as an open-celled foam material (e.g., a sponge material). The wound filler 207 can be configured to provide fluid transport between the wound 205 and a negative pressure source 208. The negative pressure source 208 can comprise a pressure pump, such as a vacuum pump. The negative pressure source 208 can be coupled to the wound cover 202 through a conduit 210 (e.g., tube). The negative pressure source 208 can be configured to apply negative pressure to the sealable space 204 through the conduit 210. Arrows in FIG. 2 indicate how liquid and/or gas may travel from the wound 205 towards the negative pressure source 208 via the wound cover 202, the suction member 203, and the conduit 210.

By way of example, the negative pressure source 208 can be configured to provide a negative pressure, the absolute value of which is greater than or equal to a threshold value. As an illustration, the threshold value in such embodiments can be at least 20 mmHg. The negative pressure source 208 can be configured to provide negative pressure at one fixed threshold value. The negative pressure source 208 can be configured to provide negative pressure at multiple values which may be selected, for example, by the user and/or depending on the therapy mode. For example, the negative pressure source 208 can be configured to provide negative pressure at various values within a range. As a further example, the negative pressure source 208 can be configured to provide negative pressure at any value in certain increments from a lower limit (absolute value) to an upper limit (absolute value).

In an aspect, the negative pressure source 208 can be configured to provide negative pressure continuously during treatment. For example, the negative pressure source 208 can be configured to provide negative pressure intermittently during treatment. The negative pressure source 208 can be configured to provide negative pressure either continuously or intermittently during treatment, as selected by the user. Generally, the negative pressure source 208 can be configured to provide negative pressure at one or more values that fall within the range between about 20 mmHg and about 400 mHg (inclusive of endpoints).

For example, typical threshold values used during negative pressure wound therapy include any value in the range between about 20 mmHg and about 400 mmHg (inclusive of both endpoints), for example, about 20 mmHg, about 25 mmHg, about 50 mmHg, about 60 mmHg, about 80 mmHg, about 120 mmHg, about 200 mmHg, or about 300 mmHg. For example, in some embodiments, a negative pressure of about 80 mm Hg is used. In some embodiments, a negative pressure of about 120 mmHg is used. The selection of the appropriate values may be made, for example, by a health care provider (e.g., a clinician). The choice of appropriate negative pressure value(s) may be influenced by any or a combination of factors such as location of wound, type of wound, wound healing status, type and/or material of wound filler 207, type of dressing, patient, etc. For example, in some embodiments where gauze is used as a wound filler 207, a negative pressure of about 80 mmHg is used. As a further example, in some embodiments where a foam is used as a wound filler 207, a negative pressure of about 120 mmHg is used.

The treatment device 200 can comprise a control unit 212. The control unit 212 can comprise memory 214 and a processor 216 (e.g., microprocessor). The processor can be, in electronic communication with the negative pressure source 208. The processor 216 can be configured (e.g., via machine-readable code and hardware components) to perform any of the functionality of the treatment device 102 of FIG. 1, such as functionality associated with the treatment unit 112, the evaluation unit 114, the alert unit 116, and the network unit 118.

The processor 216 can be configured to determine a state of the negative pressure source 208. For example, the processor 216 can be configured to determine whether power is being supplied to the negative pressure source 208. The processor 216 can be configured to determine an amount of power (e.g., a power level) supplied to the negative pressure source 208. For example, the processor 216 can access a current sensor or voltage sensor. As another example, the process 216 determine whether a switch, relay, transistor, and/or the like is open or closed.

The processor 216 can be configured to determine an amount of the applied negative pressure of the vacuum pump. For example, the treatment device 200 can comprise a pressure sensor 218. The pressure sensor 218 can be coupled to (e.g., receiving pressure from) the conduit 210, as shown, or can be disposed within the negative pressure source 208, the conduit 210, the wound cover 202, the wound filler 207, the suction member 203, and/or the like. The pressure sensor 218 can comprise a pressure element configured to react to (e.g., measure) changes in pressure. The pressure element can comprise a diaphragm, piezoelectric element (e.g., plate), or other transducer.

The processor 216 can be configured to determine a patient compliance factor based on the state of the negative pressure source 208, the amount of the applied negative pressure, operation parameters, a treatment plan, and/or the like as described further herein. The processor 216 can be configured to determine a notification and/or alert indicative of the patient compliance factor as described further herein. For example, the processor 216 can determine a graphical object modifier based on the patient compliance factor.

The treatment device 200 can comprise a display 220, in electronic communication with the processor 216, configured to display a graphical object based on the graphical object modifier. For example, the graphical object can be indicative of patient compliance (e.g., the patient compliance factor), as described further herein.

The treatment device 200 can comprise a speaker 222, in electric communication with the processor 216, configured to provide an audio signal. The audio signal (e.g., approval signal, warning signal) can be selected by the processor 216 based on the patient compliance factor, the severity of the patient compliance factor, whether the patient compliance factor is negative or positive, and/or the like. For example, if the patient compliance factor and/or the severity of the patient compliance factor is above a threshold, a warning signal and/or warning message can be provided. If the patient compliance factor and/or the severity of the patient compliance factor is below a threshold an approval message and/or approval signal can be provided.

The treatment device 200 can comprise a light source 224, such as a light emitting diode, a bulb, and/or the like. The light source 224 can be configured to display a variety of colors (e.g., red, orange, green). The color, brightness, and/or signal (e.g., blinking) can be selected by the processor 216 based on the patient compliance factor, the severity of the patient compliance factor, whether the patient compliance factor is negative or positive, and/or the like.

The treatment device 200 can comprise a transceiver 226 configured to communicate with remote devices via a network. The transceiver 226 can comprise an antenna, analog-to-digital converter, digital-to-analog converter, and/or the like. The transceiver 226 can comprise the network unit 118 of FIG. 1.

FIG. 3A and FIG. 3B illustrate modification of example graphical objects. FIG. 3A illustrates modification of an example tree graphical object. The tree graphical object can appear to grow and/or mature over time as the treatment is applied properly (e.g., within specified operation parameters, for a specified amount time, above a threshold pressure). The tree graphical object can appear to shrink and/or wither over time as the treatment is not applied properly (e.g., not within specified operation parameters, not for the minimum amount of time, not above a threshold pressure). A series of displays illustrate an example progression. At display 302, the patient has started the treatment and the tree graphical object appears small. At display 304, the tree graphical object is modified (e.g., based on a graphical object modifier) to increase the size and/or maturity of the tree after the treatment continues to match the treatment plan and/or operation parameters. At display 306, the tree graphical object is modified again (e.g., based on a graphical object modifier) to increase the size and/or maturity of the tree after the treatment continues to match the treatment plan and/or operation parameters. At display 308, the tree graphical object is modified (e.g., based on a graphical object modifier) to decrease the size and/or show the tree as withered after the treatment no longer continues to match the treatment plan and/or operation parameters.

FIG. 3B illustrates modification of an example face graphical object. The face graphical object can appear to show a happy expression (e.g., smile) over time as the treatment is applied properly (e.g., within specified operation parameters, for a specified amount time, above a threshold pressure). The face graphical object can appear to show a sad expression (e.g., frown) over time as the treatment is not applied properly (e.g., not within specified operation parameters, not for the minimum amount of time, not above a threshold pressure). A series of displays illustrate an example progression. At display 310, the patient has failed to apply the treatment properly (e.g., as prescribed) and the face graphic object shows a sad expression. At display 312, the face graphical object is modified (e.g., based on a graphical object modifier) to show a neutral expression after the treatment begins to match the treatment plan and/or operation parameters. At display 314, the face graphical object is modified again (e.g., based on a graphical object modifier) to show a happy expression after the treatment continues to match the treatment plan and/or operation parameters. At display 316, the face graphical object is modified (e.g., based on a graphical object modifier) to appear neutral after the treatment no longer continues to match the treatment plan and/or operation parameters.

Figure 4:
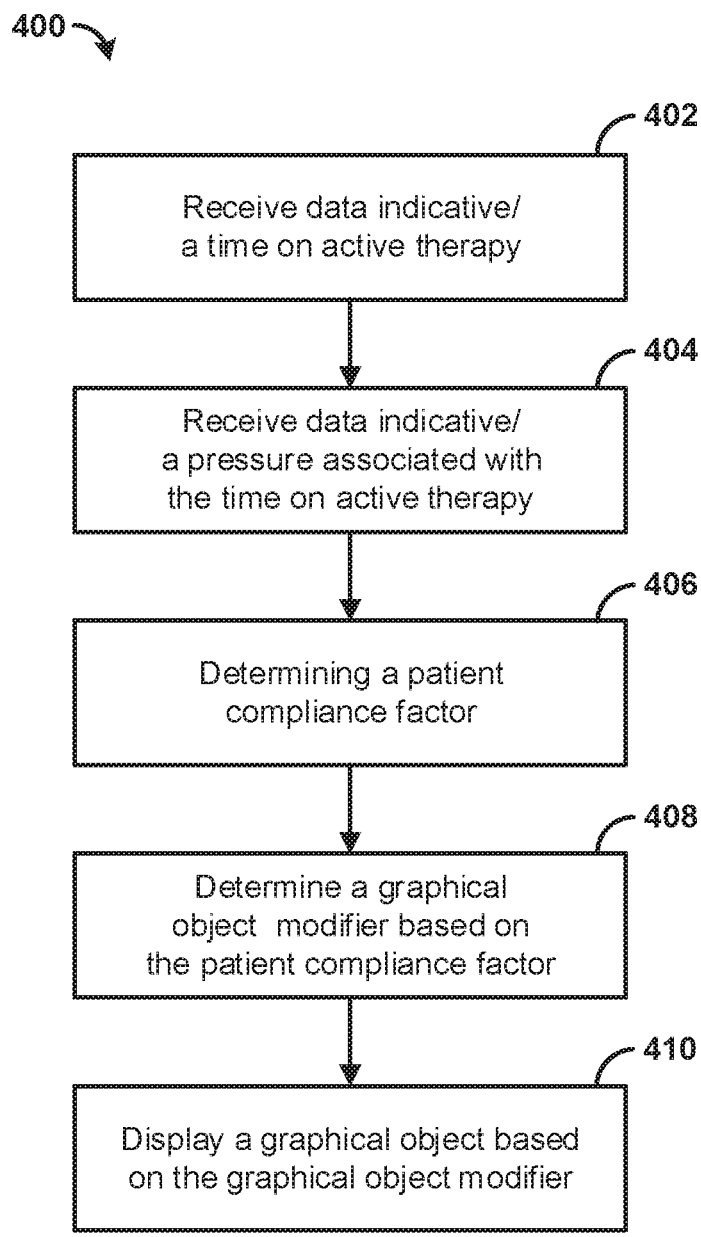
FIG. 4 is a flowchart illustrating an example method for managing treatment of a patient.

FIG. 4 is a flowchart illustrating an example method 400 for managing treatment of a patient. At step 402, data indicative of a time on active therapy can be received. The time on active therapy can comprise a time during which the therapy is being applied to the patient.

In an aspect, the data indicative of the time on active therapy can be received by a first device. The first device can comprise a device configured to apply a therapy, such as a negative pressure wound treatment apparatus. The first device can be configured to apply a negative pressure to a wound of a patient. The data indicative of the time on active therapy can be received by a second device. The second device can comprise a patient monitoring device, such as a device monitored by a health care provider. The second device can be remote from the first device. For example, the second device can receive the data from the first device and/or a third device. The data indicative of the time on active therapy can be received by a third device. The third device can comprise a user device. The user device can be a computer, tablet device, smart device (e.g., smart phone, smart apparel, smart watch, smart glasses), laptop device, mobile device, home health monitoring device, and/or the like. The third device can receive the data from the first device (e.g., via WiFi, Bluetooth®, or other wireless or weird communication link).

At step 404, data indicative of a pressure associated with the time on active therapy can be received (e.g., by the first device, second device, and/or third device). For example, the data indicative of the pressure can be received from a pressure sensor. Receiving the data indicative of the time on active therapy can comprise receiving a first periodic timestamp and an indication of a state of a vacuum pump (e.g., of the first device) associated with the first periodic timestamp. Receiving the data indicative of the pressure associated with the time on active therapy can comprise receiving a second periodic timestamp and an indication of a pressure applied by the vacuum pump associated with the second periodic timestamp.

At step 406, a patient compliance factor can be determined (e.g., by the first device, second device, and/or third device). The patient compliance factor can comprise a measure of compliance with a treatment plan (e.g., schedule, therapy plan). For example, the treatment plan can be a prescribed treatment plan (e.g., prescribed or ordered by a health care professional). The treatment plan can comprise specific times (e.g., start times, end times, duration) for applying a treatment (e.g., therapy). The treatment plan can comprise an amount of time to apply treatment during a time period. The treatment plan can comprise operation parameters for applying the treatment via the first device. The operation parameters can comprise a pressure level (e.g., negative pressure level), power level, configuration settings (e.g., signal to use to apply negative pressure), and/or the like.

For example, the patient compliance factor can be determined based on the data indicative of the time on active therapy. The patient compliance factor can be determined based on the data indicative of the pressure associated with the time on active therapy. In an aspect, determining the patient compliance factor based on the data indicative of the time on active therapy and/or the data indicative of the pressure associated with the time on active therapy can comprise performing the following step in any appropriate order. In a first step, the first periodic timestamp can be matched with the second periodic timestamp. In a second step, if the first periodic timestamp matches the second periodic timestamp, it can be determined if the state of the vacuum pump associated with the first periodic timestamp is an active state. In an third step, it can be determined if the pressure applied by the vacuum pump associated with the second periodic timestamp is within a prescribed pressure. In a fourth step, if the state of the vacuum pump associated with the first periodic timestamp is an active state and/or if the pressure applied by the vacuum pump of associated with the second periodic timestamp is within the prescribed pressure, the patient compliance factor can be updated to indicate positive patient compliance. If the state of the vacuum pump associated with the first periodic timestamp is an inactive state and/or if the pressure applied by the vacuum pump associated with the second periodic timestamp is not within the prescribed pressure, the patient compliance factor can be updated to indicate negative patient compliance.

At step 408, a graphical object modifier can be determined (e.g., by the first device, second device, and/or third device) based on the patient compliance factor. For example, determining the graphical object modifier based on the patient compliance factor can comprise adjusting one or more parameters indicative of one or more of, a size, a color, and a shape of the graphical object. By way of explanation, adjusting the one or more parameters indicative of one or more of, the size, the color, and the shape of the graphical object can comprise performing one or more of the following steps in any appropriate order. In a first step, a plurality of possible values for each of the one or more parameters can be determined. In a second step, determining which of the plurality of possible values for each of the one or more parameters are associated with a positive patient compliance factor and which of the plurality of possible values for each of the one or more parameters are associated with a negative patient compliance factor can be performed. In a third step, a value of the one or more parameters can be increased or decreased based on the plurality of possible values and whether the patient compliance factor is a positive patient compliance factor or a negative patient compliance factor.

At step 410, a graphical object based on the graphical object modifier can be displayed (e.g., by the first device, second device, and/or third device). For example, the graphical object can be displayed by a display of the first device. The graphical object can represent the patient compliance factor. The graphical object may appear differently based on whether the patient compliance factor is negative or positive. For example, a positive compliance factor can be represented by growth and/or maturing of an object, such as a plant (e.g., tree). A negative compliance factor can be represented by shrinking or withering of the object. As another example, a positive compliance factor can be represented by a face expressing approval and/or happiness (e.g., smiley face). The negative compliance factor can be represented by a face expressing neutrality, disapproval, and/or sadness.

In an aspect, the method 400 can further comprise determining (e.g., by the first device, second device, and/or third device) an audio signal based on the patient compliance factor. The audio signal can be emitted (e.g., sounded, played, from a speaker). For example, the audio signal can be emitted from the first device (e.g., a speaker integrated into or connected to the device). As another example, the audio signal can be emitted from the second device and/or third device.

In an aspect, the method 400 can further comprise establishing (e.g., generating, storing data within) a data store, such as a database (e.g., a patient compliance database), data file, and/or the like. The data store can comprise an association of a periodic timestamp related to an state (e.g., inactive, active, partially active) of the first device and one or more of a plurality of cause indicators. The plurality of cause indicators can indicate at least one of the vacuum pump being switched off or paused, an air or fluid leakage (e.g., inadequate dressing seal, connectors disconnected, damaged system components resulting in air leaks into the system), a loss of power (e.g., battery depleted or AC mains disconnected), a canister not being engaged, the canister being full, a system error, an air blockage, a reduced vacuum pressure (e.g., only partial vacuum being applied), a combination thereof, and/or the like.

Figure 5:
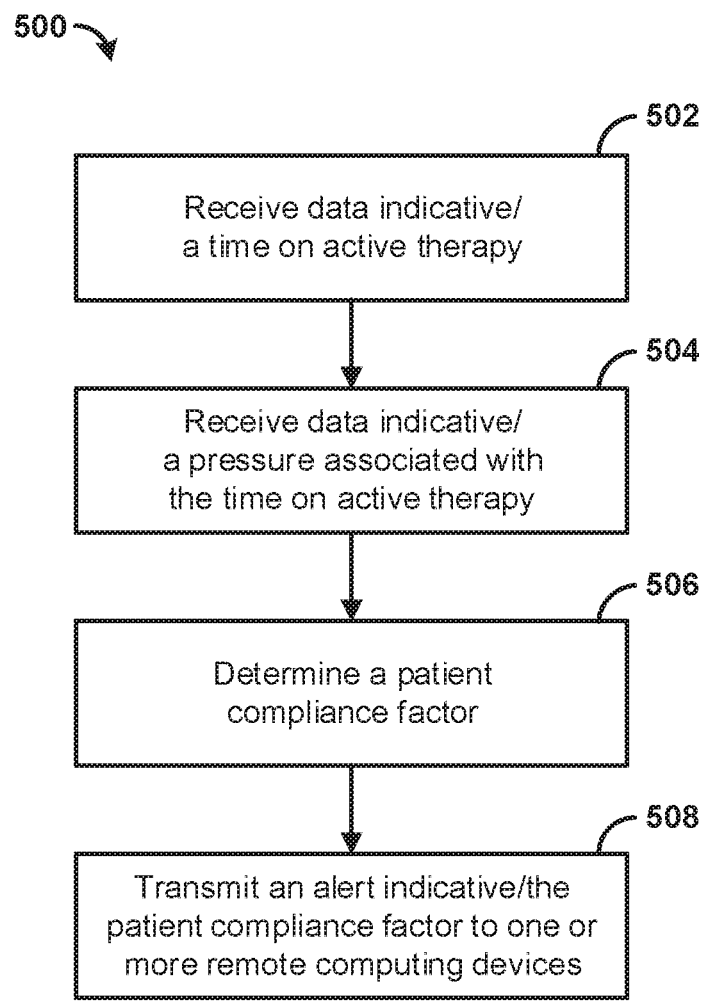
FIG. 5 is a flowchart illustrating another example method for managing treatment of a patient.

FIG. 5 is a flowchart illustrating another example method 400 for managing treatment of a patient. At step 502, data indicative of a time on active therapy can be received. The time on active therapy can comprise a time during which the therapy is being applied to the patient.

In an aspect, the data indicative of the time on active therapy can be received by a first device. The first device can comprise a device configured to apply a therapy, such as a negative pressure wound treatment apparatus. The first device can be configured to apply a negative pressure to a wound of a patient. The data indicative of the time on active therapy can be received by a second device. The second device can comprise a patient monitoring device, such as a device monitored by a health care provider. The second device can be remote from the first device. For example, the second device can receive the data from the first device and/or a third device. The data indicative of the time on active therapy can be received by a third device. The third device can comprise a user device. The user device can be a computer, tablet device, smart device (e.g., smart phone, smart apparel, smart watch, smart glasses), laptop device, mobile device, home health monitoring device, and/or the like. The third device can receive the data from the first device (e.g., via WiFi, Bluetooth®, or other wireless or weird communication link).

In an aspect, receiving the data indicative of a time on active therapy can comprise receiving a first periodic timestamp and an indication of a state of a vacuum pump of the first device (e.g., the therapy device, the negative pressure wound treatment apparatus) associated with the first periodic timestamp.

At step 504, data indicative of a pressure associated with the time on active therapy can be received (by the first device, second device, and/or third device). For example, the data indicative of the pressure can be received from a pressure sensor. Receiving the data indicative of the pressure associated with the time on active therapy can comprise receiving a second periodic timestamp and an indication of a pressure applied by the vacuum pump of the first device associated with the second periodic timestamp.

At step 506, a patient compliance factor can be determined (e.g., by the first device, second device, and/or third device). The patient compliance factor can be determined based on the data indicative of the time on active therapy and/or the data indicative of the pressure associated with the time on active therapy.

In an aspect, determining the patient compliance factor based on the data indicative of the time on active therapy and/or the data indicative of the pressure associated with the time on active therapy can comprise performing one or more of the following steps in any appropriate order. In a first step, the first periodic timestamp can be matched with the second periodic timestamp. In a second step, if the first periodic timestamp matches the second periodic timestamp, it can be determined if the state of the vacuum pump associated with the first periodic timestamp is an active state. In a third step, it can be determined if the pressure applied by the vacuum pump associated with the second periodic timestamp is within a prescribed pressure. In a fourth step, if the state of the vacuum pump associated with the first periodic timestamp is an active state and if the pressure applied by the vacuum pump associated with the second periodic timestamp is within the prescribed pressure, the patient compliance factor can be updated to indicate positive patient compliance. If the state of the vacuum pump associated with the first periodic timestamp is an inactive state or if the pressure applied by the vacuum pump of the first device associated with the second periodic timestamp is not within the prescribed pressure, the patient compliance factor can be updated to indicate negative patient compliance.

At step 508, an alert indicative of the patient compliance factor can be transmitted (e.g., by the first device, second device, and/or third device) to one or more remote computing devices. For example, the alert can be transmitted between components of the first device. The alert can be transmitted from the first device to the second device and/or third device. The alert can be transmitted via a network (e.g., wireless network), a communication link (e.g., wireless communication link), and/or the like.

In an aspect, transmitting the alert indicative of the patient compliance factor to the one or more remote computing devices can comprise performing one or more of the following steps in any appropriate order. In a first step, a severity of the patient compliance factor can be determined. In a second step, one or more recipients can be selected based on the severity of the patient compliance factor. In a third step, a mode of communication associated with each of the selected one or more recipients can be identified. In a fourth step, the alert can be transmitted to the selected one or more recipients according to the associated mode of communication.

By way of further explanation, determining the severity of the patient compliance factor can comprise performing one or more of the following steps in any appropriate order. In a first step, it can be determined if the patient compliance factor indicates a negative compliance or a positive compliance. In a second step, a length of time the patient compliance factor has indicated a negative compliance or a positive compliance can be determined. In a third step, it can be determined that the patient compliance factor indicates a high risk if the patient compliance factor indicates a negative compliance and the length of time the patient compliance factor has indicated a negative compliance exceeds a predetermined threshold. It can be determined that the patient compliance factor indicates a low risk if the patient compliance factor indicates a positive compliance and the length of time the patient compliance factor has indicated a positive compliance exceeds a predetermined threshold.

In an aspect, the method 500 can further comprise determining (e.g., by the first device, second device, and/or third device) an audio signal based on the patient compliance factor. The audio signal can be emitted (e.g., sounded, played, from a speaker). For example, the audio signal can be emitted from the first device (e.g., a speaker integrated into or connected to the device). As another example, the audio signal can be emitted from the second device and/or third device.

In an aspect, the method 500 can further comprise establishing (e.g., generating, storing data within) a data store, such as a database (e.g., a patient compliance database) or data file. The data store can comprise an association of a periodic timestamp related to an state (e.g., inactive, active, partially active) of the first device and one or more of a plurality of cause indicators. The plurality of cause indicators can indicate at least one of the vacuum pump being switched off or paused, an air or fluid leakage (e.g., inadequate dressing seal, connectors disconnected, damaged system components resulting in air leaks into the system), a loss of power (e.g., battery depleted or AC mains disconnected), a canister not being engaged, the canister being full, a system error, an air blockage, a reduced vacuum pressure (e.g., only partial vacuum being applied), a combination thereof, and/or the like.

Figure 6:
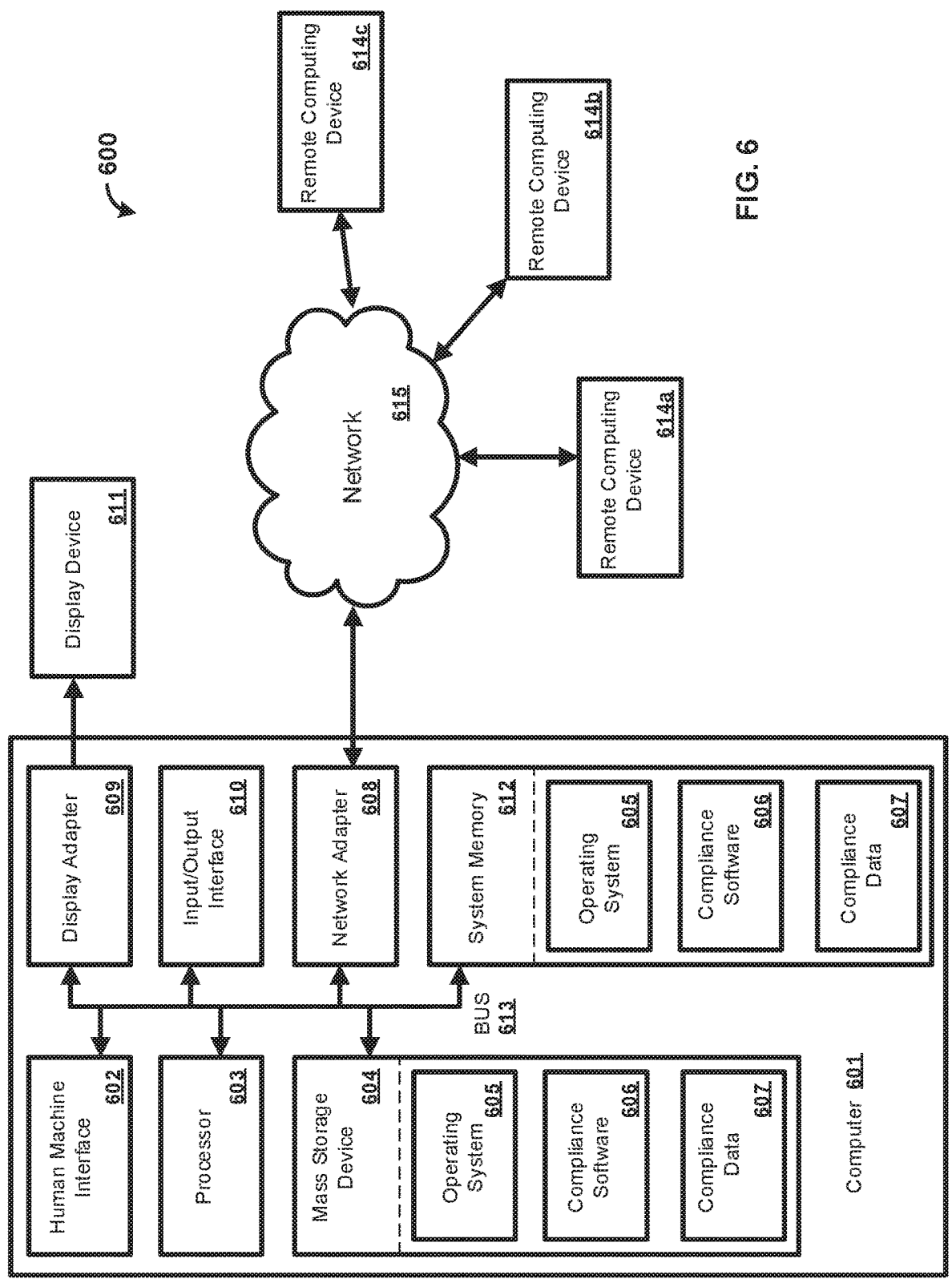
FIG. 6 is a block diagram illustrating an example computing device in which the present methods and systems can operate.

In an exemplary aspect, the methods and systems can be implemented on a computer 601 as illustrated in FIG. 6 and described below. By way of example, the treatment device 102, the patient monitoring device 104, the patient device 106, and/or the third party device 108 of FIG. 1 can be one or more computers as illustrated in FIG. 6. The treatment device 200 of FIG. 2 can be a computer as illustrated in FIG. 6. Similarly, the methods and systems disclosed can utilize one or more computers to perform one or more functions in one or more locations. FIG. 6 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 601. The components of the computer 601 can comprise, but are not limited to, one or more processors 603, a system memory 612, and a system bus 613 that couples various system components including the one or more processors 603 to the system memory 612. The system can utilize parallel computing.

The system bus 613 represents one or more of several possible types of bus structures, including a memory bus or memory controller, a peripheral bus, an accelerated graphics port, or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCM-CIA), Universal Serial Bus (USB) and the like. The system bus 613, and all buses specified in this description can also be implemented over a wired or wireless network connection and each of the subsystems, including the one or more processors 603, a mass storage device 604, an operating system 605, compliance software 606, compliance data 607, a network adapter 608, the system memory 612, an Input/Output Interface 610, a display adapter 609, a display device 611, and a human machine interface 602, can be contained within one or more remote computing devices 614a,b,c at physically separate locations, connected through buses of this form, in effect implementing a fully distributed system.

The computer 601 typically comprises a variety of computer readable media. Exemplary readable media can be any available media that is accessible by the computer 601 and comprises, for example and not meant to be limiting, both volatile and non-volatile media, removable and non-removable media. The system memory 612 comprises computer readable media in the form of volatile memory, such as random access memory (RAM), and/or non-volatile memory, such as read only memory (ROM). The system memory 612 typically contains data such as the compliance data 607 and/or program modules such as the operating system 605 and the compliance software 606 that are immediately accessible to and/or are presently operated on by the one or more processors 603.

In another aspect, the computer 601 can also comprise other removable/non-removable, volatile/non-volatile computer storage media. By way of example, FIG. 6 illustrates the mass storage device 604 which can provide non-volatile storage of computer code, computer readable instructions, data structures, program modules, and other data for the computer 601. For example and not meant to be limiting, the mass storage device 604 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 604, including by way of example, the operating system 605 and the compliance software 606. Each of the operating system 605 and the compliance software 606 (or some combination thereof) can comprise elements of the programming and the compliance software 606. The compliance data 607 can also be stored on the mass storage device 604. The compliance data 607 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 601 via an input device (not shown). Examples of such input devices comprise, but are not limited to, a keyboard, pointing device (e.g., a "mouse"), a microphone, a joystick, a scanner, tactile input devices such as gloves, and other body coverings, and the like These and other input devices can be connected to the one or more processors 603 via the human machine interface 602 that is coupled to the system bus 613, but can be connected by other interface and bus structures, such as a parallel port, game port, an IEEE 1394 Port (also known as a Firewire port), a serial port, or a universal serial bus (USB).

In yet another aspect, the display device 611 can also be connected to the system bus 613 via an interface, such as the display adapter 609. It is contemplated that the computer 601 can have more than one display adapter 609 and the computer 601 can have more than one display device 611. For example, the display device 611 can be a monitor, an LCD (Liquid Crystal Display), or a projector. In addition to the display device 611, other output peripheral devices can comprise components such as speakers (not shown) and a printer (not shown) which can be connected to the computer 601 via the Input/Output Interface 610. Any step and/or result of the methods can be output in any form to an output device. Such output can be any form of visual representation, including, but not limited to, textual, graphical, animation, audio, tactile, and the like. The display device 611 and computer 601 can be part of one device, or separate devices.

The computer 601 can operate in a networked environment using logical connections to one or more remote computing devices 614a,b,c. By way of example, a remote computing device can be a personal computer, portable computer, smartphone, a server, a router, a network computer, a peer device or other common network node, and so on. Logical connections between the computer 601 and a remote computing device 614a,b,c can be made via a network 615, such as a local area network (LAN) and/or a general wide area network (WAN). Such network connections can be through the network adapter 608. The network adapter 608 can be implemented in both wired and wireless environments. Such networking environments are conventional and commonplace in dwellings, offices, enterprise-wide computer networks, intranets, and the Internet.

For purposes of illustration, application programs and other executable program components such as the operating system 605 are illustrated herein as discrete blocks, although it is recognized that such programs and components reside at various times in different storage components of the computer 601, and are executed by the one or more processors 603 of the computer. An implementation of the compliance software 606 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
   receiving, by a negative pressure wound treatment apparatus, data indicative of an amount of time that a negative pressure source associated with the negative pressure wound treatment apparatus was active and an amount of pressure applied by the negative pressure source during a period of time;
   determining, by the negative pressure wound treatment apparatus, a patient compliance factor based on: the amount of time and the amount of pressure, wherein the patient compliance factor is indicative of a current compliance with a treatment plan;
   based on a determination of continuing compliance with or a failure to comply with the treatment plan, determining, by the negative pressure wound treatment apparatus, based on the patient compliance factor, a graphical object modifier associated with a first graphical object previously output via a display of the negative pressure wound treatment apparatus, wherein the first graphical object is indicative of a previous compliance with the treatment plan based on a previous amount of time the negative pressure source was active and a previous amount of pressure applied by the negative pressure source during a previous period of time;
   outputting, via the display of the negative pressure wound treatment apparatus, based on the first graphical object and the graphical object modifier, a second graphical object, wherein the second graphical object comprises at least one portion that differs from the first graphical object, wherein the portion that differs from the first graphical object is indicative of a difference between at least one of: the previous amount of time and the amount of time indicated by the data or the previous amount of pressure and the amount of pressure indicated by the data;
   sending, by the negative pressure wound treatment apparatus, to a computing device associated with a healthcare provider, an indication of the current compliance with the treatment plan; and
   receiving, by the negative pressure wound treatment apparatus, an update to the treatment plan.

2. The method of claim 1, wherein receiving, by the negative pressure wound treatment apparatus, the data indicative of the amount of time that the negative pressure source was active and an amount pressure applied by the negative pressure source during a period of time comprises: receiving a first periodic timestamp associated with the amount of time.

3. The method of claim 2, further comprising: receiving a second periodic timestamp associated with the amount of pressure.

4. The method of claim 3, wherein determining, by the negative pressure wound treatment apparatus, the patient compliance factor comprises:
matching the first periodic timestamp with the second periodic timestamp, wherein the amount of time indicated by the data comprises a duration of time that the negative pressure wound treatment apparatus was operating in an active state; and
determining that the amount of pressure applied by the negative pressure source is within a prescribed pressure of the treatment plan, wherein the second graphical object is indicative of positive compliance with the treatment plan.

5. The method of claim 3, wherein determining, by the negative pressure wound treatment apparatus, the patient compliance factor comprises:
matching the first periodic timestamp with the second periodic timestamp, wherein the amount of time indicated by the data comprises a duration of time that the negative pressure wound treatment apparatus was operating in a partially active state; and
determining that the amount of pressure applied by the negative pressure source is not within a prescribed pressure of the treatment plan, wherein the second graphical object is indicative of negative compliance with the treatment plan.

6. The method of claim 1, wherein determining, by the negative pressure wound treatment apparatus, the graphical object modifier comprises adjusting one or more parameters indicative of one or more of a size, a color, or a shape of the second graphical object.

7. The method of claim 6, wherein adjusting the one or more parameters comprises:
adjusting, based on the current compliance with the treatment plan indicated by the patient compliance factor, the one or more parameters.

8. The method of claim 1, further comprising:
determining, by the negative pressure wound treatment apparatus, an audio signal based on the patient compliance factor; and
emitting, by the negative pressure wound treatment apparatus, the audio signal.

9. The method of claim 8, wherein the audio signal is indicative of the current compliance with the treatment plan.

10. A method comprising:
receiving, by a negative pressure wound treatment apparatus, data indicative of an amount of time that a negative pressure source associated with the negative pressure wound treatment apparatus was active and an amount of pressure applied by the negative pressure source during a period of time;
determining, by the negative pressure wound treatment apparatus, a patient compliance factor based on: the amount of time and the amount of pressure, wherein the patient compliance factor is indicative of a current compliance with a treatment plan;
based on a determination of continuing compliance with or a failure to comply with the treatment plan, sending, by the negative pressure wound treatment apparatus, and based on the patient compliance factor, an alert to one or more remote computing devices, wherein the alert comprises a modified graphical object indicative of the current compliance with the treatment plan, and wherein the modified graphical object is output by the negative pressure wound treatment apparatus and comprises at least one portion that indicates a difference between at least one of: a previous amount of time and the amount of time indicated by the data or the previous amount of pressure and the amount of pressure indicated by the data;
sending, by the negative pressure wound treatment apparatus to a computing device associated with a healthcare provider, an indication of the current compliance with the treatment plan; and
receiving, by the negative pressure wound treatment apparatus, an update to the treatment plan.

11. The method of claim 10, wherein receiving, by the negative pressure wound treatment apparatus, the data indicative of the amount of time that the negative pressure source was active and an amount pressure applied by the negative pressure source during a period of time comprises: receiving a first periodic timestamp associated with the amount of time.

12. The method of claim 11, further comprising: receiving a second periodic timestamp associated with the amount of pressure.

13. The method of claim 12, wherein determining, by the negative pressure wound treatment apparatus, the patient compliance factor comprises:
matching the first periodic timestamp with the second periodic timestamp, wherein the amount of time indicated by the data comprises a duration of time that the negative pressure wound treatment apparatus was operating in an active state; and
determining that the amount of pressure applied by the negative pressure source is within a prescribed pressure of the treatment plan.

14. The method of claim 12, wherein determining, by the negative pressure wound treatment apparatus, the patient compliance factor comprises:
matching the first periodic timestamp with the second periodic timestamp, wherein the amount of time indicated by the data comprises a duration of time that the negative pressure wound treatment apparatus was operating in a partially active state; and
determining that the amount of pressure applied by the negative pressure source is not within a prescribed pressure, wherein the modified graphical object is indicative of negative compliance with the treatment plan.

15. The method of claim 10, wherein sending, by the negative pressure wound treatment apparatus, the alert comprises:
determining a severity of the patient compliance factor;
selecting one or more recipients based on the severity of the patient compliance factor;
identifying a mode of communication associated with each of the selected one or more recipients; and
sending the alert to the one or more recipients according to the mode of communication.

16. The method of claim 15, wherein determining the severity of the patient compliance factor comprises:
determining a length of time the patient compliance factor has indicated a negative compliance with the treatment plan; and
determining, based on the length of time exceeding a predetermined threshold, the severity of the patient compliance factor.

17. The method of claim 15, wherein determining the severity of the patient compliance factor comprises:
  determining a length of time the patient compliance factor has indicated a positive compliance with the treatment plan; and
  determining, based on the length of time exceeding a predetermined threshold, the severity of the patient compliance factor.

18. The method of claim 10, further comprising:
  determining, by the negative pressure wound treatment apparatus, an audio signal based on the patient compliance factor; and
  emitting, by the negative pressure wound treatment apparatus, the audio signal.

19. The method of claim 18, wherein the audio signal is indicative of the current compliance with the treatment plan.

20. An apparatus comprising:
  a wound cover configured for creating a sealable space defined in part by a wound surface;
  a vacuum pump, coupled to the wound cover though a tube, wherein the vacuum pump is configured to apply an amount of negative pressure to the sealable space through the tube;
  at least one processor, in communication with the vacuum pump, wherein the at least one processor is configured to:
    determine an amount of time that the vacuum pump was active and applying the amount of negative pressure during a period of time,
    determine a patient compliance factor based on: the amount of time and the amount of negative pressure, wherein the patient compliance factor is indicative of a current compliance with a treatment plan, and
    based on a determination of continuing compliance with or a failure to comply with the treatment plan, determine, based on the patient compliance factor, a graphical object modifier associated with a first graphical object previously output, wherein the first graphical object is indicative of a previous compliance with the treatment plan based on a previous amount of time the negative pressure source was active and a previous amount of negative pressure applied during a previous period of time; and
  a display, in communication with the at least one processor, configured to display:
    the first graphical object indicative of the previous compliance with the treatment plan, and
    based on the first graphical object and the graphical object modifier, a second graphical object comprising at least one a portion that differs from the first graphical object, wherein the at least one portion that differs from the first graphical object is indicative of a difference between at least one of: the previous amount of time and the amount of time or the previous amount of negative pressure and the amount of pressure,
  wherein the at least one processor is further configured to:
    cause an indication of the current compliance with the treatment plan to be sent to a computing device associated with a healthcare provider; and
    receive an update to the treatment plan.

21. The apparatus of claim 20, wherein the at least one processor is further configured to:
  associate a first periodic timestamp with the amount of time that the vacuum pump was active and applying the amount of negative pressure during the period of time; and
  associate a second periodic timestamp with the amount of negative pressure.

22. The apparatus of claim 21, wherein the at least one processor is configured to determine the patient compliance factor by performing steps comprising:
  matching the first periodic timestamp with the second periodic timestamp, wherein the amount of time comprises a duration of time that the negative pressure wound treatment apparatus was operating in an active state; and
  determining that the amount of negative pressure applied by the vacuum pump associated with the second periodic timestamp is within a prescribed pressure of the treatment plan, wherein the second graphical object is indicative of positive compliance with the treatment plan.

23. The apparatus of claim 22, further comprising a communication device configured to send an alert indicative of the patient compliance factor to one or more remote computing devices.

24. The apparatus of claim 23, wherein the alert comprises an audio signal.

25. The apparatus of claim 23, wherein the alert is communicated by adjusting one or more parameters indicative of one or more of a size, a color, or a shape of the second graphical object.

26. The apparatus of claim 21, wherein the at least one processor is configured to determine the patient compliance factor by performing steps comprising:
  matching the first periodic timestamp with the second periodic timestamp, wherein the amount of time comprises a duration of time that the negative pressure wound treatment apparatus was operating in a partially active state; and
  determining that the amount of negative pressure applied by the vacuum pump is not within a prescribed pressure of the treatment plan, wherein the second graphical object is indicative of negative compliance with the treatment plan.

27. The apparatus of claim 21, wherein the at least one processor is further configured to adjust one or more parameters indicative of one or more of, a size, a color, or a shape of the second graphical object, and wherein the graphical object modifier is determined based on the adjusted one or more parameters.

28. The apparatus of claim 20, wherein the at least one processor is configured to:
  determine a severity of the patient compliance factor;
  select one or more recipients based on the severity of the patient compliance factor;
  identify a mode of communication associated with each of the selected one or more recipients; and
  cause an alert indicative of the current compliance with the treatment plan to be sent to the selected one or more recipients according to the mode of communication.

29. The apparatus of claim 24, wherein the alert is indicative of the current compliance with the treatment plan.

* * * * *